United States Patent [19]

Mizushima

[11] Patent Number: 5,362,491
[45] Date of Patent: Nov. 8, 1994

[54] MODIFIED BIOLOGICALLY ACTIVE PROTEIN COMPOSITION

[75] Inventor: Yutaka Mizushima, 4-25-20, Daida, Setagaya-ku, Tokyo, Japan

[73] Assignees: Yutaka Mizushima; Asahi Glass Company Ltd.; Seikagaku Kogyo Co., Ltd., all of Tokyo, Japan

[21] Appl. No.: 190,451

[22] Filed: Feb. 2, 1994

Related U.S. Application Data

[62] Division of Ser. No. 832,585, Feb. 7, 1992, Pat. No. 5,310,958, which is a division of Ser. No. 547,039, Jul. 2, 1990, Pat. No. 5,109,118.

[30] Foreign Application Priority Data

Jul. 6, 1989 [JP] Japan ................... 1-174371
Nov. 29, 1989 [JP] Japan ................... 1-310056

[51] Int. Cl.⁵ .............. A61K 37/26; A61K 39/00
[52] U.S. Cl. ........................... 424/180.1; 514/3; 514/12; 435/177; 435/188; 530/324; 530/345; 530/391.5; 530/391.7; 530/391.9; 530/409; 530/410; 424/182.1
[58] Field of Search ............... 435/177, 188; 530/391.5, 391.7, 391.9, 410, 409, 303, 324, 345, 350; 424/85.8, 94.3; 514/3, 12

[56] References Cited

U.S. PATENT DOCUMENTS 5,120,710  6/1992  Liedtke .................. 514/3

OTHER PUBLICATIONS

Tan, Diss. Abstr. B, 27(12), pp. 4241–4242 (1967).

*Primary Examiner*—Michael G. Wityshyn
*Assistant Examiner*—C. Sayala
*Attorney, Agent, or Firm*—Oblon, Spivak, McClelland, Maier & Neustadt

[57] ABSTRACT

A composition which comprises a modified biologically active protein consisting essentially of a biologically active protein bonded to lecithin via a covalent linkage and a protein inhibitor which does not inhibit the modified biologically active protein.

11 Claims, No Drawings

MODIFIED BIOLOGICALLY ACTIVE PROTEIN COMPOSITION

The present application is a divisional of copending application Ser. No. 07/832,585 filed on Feb. 7, 1992, now U.S. Pat. No. 5,310,958, which is a divisional of application Ser. No. 07/547,039 filed Jul. 2, 1990 now U.S. Pat. No. 5,109,118.

The present invention relates to a modified biologically active protein.

Attempts to improve pharmacological effects and reduce side effects have been made since long ago. As one of recent attempts, a drug delivery system (DDS) may be mentioned. DDS is an attempt to let a drug transmigrate to a necessary site preferably selectively for a necessary period of time, so that the pharmacological effects be improved, and general side effects be substantially reduced. Various types are available as carriers for DDS. Among them, lyposome and lipid microspheres may be mentioned as typical examples. Lyposome is prepared by dissolving a natural lipid such as lecithin or cholesterol in an organic solvent, then dispersing it in water by e.g. ultrasonic treatment, and sealing a drug therein. Whereas, lipid microspheres are prepared by suspending soybean oil in water together lecithin, whereby lecithin constitutes the surface and drug is sealed in. In each case, the drug is sealed in primarily by physical bond. Lyposome has a drawback that the stability is poor. Whereas, in the case of lipid microspheres, the drug to be sealed in must be lipid-soluble, and it is further required to employ a special apparatus for the production.

The present inventors have studied a technique which is entirely different from such conventional techniques and yet is capable of providing excellent effects, and as a result, they have arrived at the present invention.

The present invention provides a modified biologically active protein consisting essentially of a biologically active protein bonded to lecithin via a chemical linkage.

This lecithin-bonded modified biologically active protein is remarkably different from the biologically active protein in the distribution in vivo and in the cell affinity. Accordingly, an improvement in the pharmacological activities of a biologically active protein, a reduction of side effects and promotion of the absorption, can be expected.

Now, the present invention will be described in detail with reference to the preferred embodiments.

The modified biologically active protein of the present invention can be obtained by bonding to a biologically active protein at least one lecithin derivative having a chemical linking agent bonded to a residue of lysolecithin (represented by B). Such a modified biologically active protein is represented by the following formula (I), wherein B is a residue of lysolecithin having a hydroxyl group at the 2-position glycerol, with the hydrogen atom of said hydroxyl group removed, as shown by the following formula (II):

$$A(X-B)_k \qquad (I)$$

wherein A is a residue of the biologically active protein, B is a residue of lysolecithin having a hydroxyl group at the 2-position of glycerol, with the hydrogen atom of said hydroxyl group removed, X is the chemical linkage, and k is a bond number of at least 1.

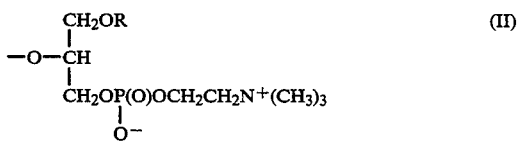

(II)

In the above formula (II), R is a fatty acid residue (an acyl group), preferably a saturated or unsaturated fatty acid residue having from 8 to 30 carbon atoms. Particularly preferred is a saturated fatty acid residue having from 14 to 22 carbon atoms, such as a myristoyl group, a palmitoyl group, or a stearoyl group. Most preferred is a palmitoyl group as an acyl group of typical lecithin. In the formula (I), X is a chemical linkage of an organic group linking A and B after the chemical linking reaction as described below.

The chemical linking agent is preferably bonded to the above lysolecithin residue by an ester bond. The other end of the chemical linking agent has a functional group which is capable of directly bonding to a functional group such as an amino group, an amide group or a carboxyl group of the biologically active protein. Otherwise, it has a functional group capable of bonding to a second chemical linking agent (which is a compound having at least two functional groups, one of which bonds to a functional group of the biologically active protein and the other of which bonds to the functional group of the first chemical linking agent). The first chemical linking agent preferably has a carboxyl group (—COOH) or an amino group (—NH$_2$) as a functional group. The lecithin derivative having such a first chemical linking agent bonded thereto, is preferably the one represented by the following formula (III):

(III)

In the above formula (III), R$^1$ is a linear or branched alkylene group having from 1 to 24 carbon atoms, preferably a linear alkylene group having from 2 to 10 carbon atoms. Z' is a reactive functional group, preferably a carboxyl group or an amino group. Z' may be a functional group capable of being converted to a carboxyl group, such as a temporarily protected carboxyl group, an amino group, a haloformyl group or an alkoxycarbonyl group. A compound of the formula (III) wherein Z' is a carboxyl group or a group capable of being converted to a carboxyl group, may be prepared by e.g. a method wherein an acid anhydride of the formula

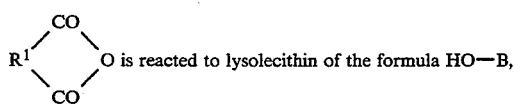

O is reacted to lysolecithin of the formula HO—B, a method in which a dicarboxylic acid half ester anhydride of the formula (R$^4$OCOR$^1$CO)$_2$O wherein R$^4$ is an alkyl group, etc. is reacted to lysolecithin, or a method wherein a dicarboxylic acid dichloride of the formula R'(COCl)$_2$ is reacted to lysolecithin. Such methods are usually conducted in a solvent, and an organic base may be present, if necessary. Otherwise, an organic base may be used as a solvent for the reactions. As a solvent for reaction, a halogenated hydrocarbon such as chloroform, may be used, and as the organic base, pyridine, piperidine or triethylamine may, for example, be used. A product having an ester group or a chloroform group, will be subjected to e.g. hydrolysis for conversion to a carboxyl group.

As a compound of the formula (III), 2-(6-aminocaproyl)lysolecithin is known [A. J. Schroit et al., Biochemistry, 22, 3616-3623 (1983)]. As will be described in hereinafter, a compound wherein Z' is an amino group may be bonded to a physiologically active protein. However, in order to improve the linkage to the biologically active protein, it is more effective to employ a compound wherein Z' is a carboxyl group. Accordingly, in a case where Z' is an amino group, it is preferred to react such a compound with a dicarboxylic acid derivative to convert the terminal functional groups to carboxyl groups. As such a dicarboxylic acid derivative, the above-mentioned anhydride or half ester anhydride dichloride, may be mentioned. By such a reaction, a lysolecithin derivative of the following formula (IV) will be obtained.

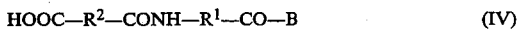

$$\text{HOOC—R}^2\text{—CONH—R}^1\text{—CO—B} \qquad (\text{IV})$$

In the above formula, $R^2$ is an alkylene group like $R^1$, which carbon number is preferably from 2 to 10.

The lecithin derivative in the present invention is not limited to the compounds of the above formulas (III) and (IV), and it may be various compounds represented by the following formula (V) having terminal carboxyl groups:

$$\text{Z—R}^3\text{—C—B} \qquad (\text{V})$$
$$\quad\ \ \ \ \|$$
$$\quad\ \ \ \ \text{O}$$

In the formula (V), Z is a carboxyl group or an activated carboxyl group as will be described hereinafter (particularly an active ester group). $R^3$ is an alkylene group such as $R^1$, or an alkylene group having a hetero atom or a carbonyl atom at an intermediate position, such as —$R_2$—CONH—$R^1$—. The following methods may, for example, be mentioned as methods for bonding a lecithin derivative of the formula (III), (IV) or (V) to a biologically active protein directly or via a second chemical linking agent.

In the compound of the formula (III), (IV), or (V), when Z or Z' is —COOH, the bonding can be conducted, for example, by a carbodiimide method or by a cyanuric chloride method. When Z' in the formula (III) is —$NH_2$, bonding can be conducted, for example, by a SPDP [N-3-succinimidyl 3-(2-pyridyldithio)propionate] method, by a carbodiimide method, or by cyanuric chloride method.

In the carbodiimide method, 1-ethyl-3-(dimethylaminopropyl)carbodiimide (EDC) or dicyclohexylcarbodiimide (DCC) may, for example, be employed, whereby a biologically active protein and lecithin will be bonded via a —CONH— linkage (—NH— is derived from an amino group of the biologically active protein). In the cyanuric chloride method, cyanuric chloride is employed, whereby a biologically active protein and lecithin will be bonded via the following linkage:

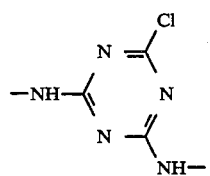

(one off —NH— groups is derived from an amino group of the biologically active protein). In the SPDP method, the two will be bonded via a —NH—CO—$CH_2CH_2$—S—S—$CH_2CH_2$CONH-linkage.

In these methods, the reactions are conducted under the conventional reaction conditions or similar conditions. For example, the above linking agent is added to lecithin and the biologically active protein, and the mixture is reacted at room temperature for from 2 to 20 hours. In such a case, lecithin is employed in a stoichiometrically substantially excess amount to the biologically active protein.

To improve the linkage to the biologically active protein, it is preferred to employ a method wherein the carboxyl group of the compound of the formula (III), (IV) or (V) having a terminal carboxyl group is activated for bonding to the biologically active protein. Such an active esterification method is known (see Izumiya et al., "Fundamentals for Peptide Analysis and Experiments" (1985) published by Maruzen K. K.). This method comprises converting the carboxyl group to a highly active ester group, and then reacting this ester to an amino group of the biologically active protein by e.g. the above-mentioned carbodiimide method, so that the lecithin derivative and the biologically active protein are bonded by an amide linkage. The active ester includes, for example, a p-nitrophenyl ester, a 1,3,5-trichlorophenyl ester, a pentafluorophenyl ester, a 2,4-dinitrophenyl ester, an N-hydroxysuccinimide ester, an N-hydroxypyridine ester, an N-hydroxy-5-norbornen-2,3-dicarboxylic acid imide ester, a 8-hydroxyquinoline ester, and a 2-hydroxypiridine ester.

The biologically active protein to be used in the present invention, may be any protein so long as it is a protein having biological activities. For example, it may be an antibody (a monoclonal antibody, or a polyclonal antibody), a peptide cell growth factor (such as NGF, EFG, FGF, CSF, EPO, interleukin 1-4, CDF ECGF TGF), insulin, cyclospolin, a growth hormone, interferon or an interferon derivative, a rheumatoid factor, a biologically active enzyme (such as urokinase, superoxide dismutase (SOD), callidinogenase, streptokinase, or elastase), a drug having a protein as a substituent, or other protein drugs (various hepatitis vaccines). The modified biologically active protein of the present invention is easy to produce as compared with the conventional products, and yet the modification is possible irrespective of the solubility of the biologically active protein.

Further, lecithin as one of the components of the present invention is a non-toxicic substance widely present in nature, and therefore, the substance of the present invention is safe also from the viewpoint of the toxicity. The modified biologically active protein of the present invention may be intravenously administered in the form of injection composition combined with a liquid carrier for injection. As such a liquid carrier, a conventional carrier such as sterilized water, a physiological saline solution, an alcohol or an aqueous alcohol solution, may be employed.

Further, this lecithin-modified biologically active protein can be orally or locally administered alone or together with a protease inhibitor which does non inhibit said biologically active protein.

Namely, the present invention provides a bioiocically active protein composition for oral or local administration, which comprises the modified biologically active protein alone, or such a protein and a protease inhibitor which does not inhibit said biologically active protein.

In one embodiment, the composition of the present invention contains, in addition to the above-mentioned lecithin-modified biologically active protein, a protease inhibitor which does not inhibit the biologically active protein. As such a protease inhibitor, various natural or synthetic protease inhibitors may be mentioned. For example, the followings may be mentioned: aprotinin, urinastatin, hirudin, soybean protease inhibitor, limabean protease inhibitor, corn protease inhibitor, gabexate mesilate, camostat mesilate and naphamostat mesilate. These inhibitors are well known and may be explained simply as follows. Aprotinin is a basic protein having a molecular weight of about 6,500 which can be extracted from bovine pancreas or lung; urinastatin is a glycoprotein having a molecular weight of about 67,000 which can be extracted from human urine; hirudin is an acidic protein having a molecular weight of about 7,000 which can be extracted from sialaden of a leech; soybean protease inhibitor is a protein having a molecular weight of about 22,000 which can be extracted from soybean; limabean protease inhibitor is a protein having a molecular weight of about 9,000 which can be extracted from limabean; gabexate mesilate ($C_{17}H_{27}N_3O_7S$) is white crystals or crystalline powder having a melting point of from 90° to 93° C.; camostat mesilate ($C_{21}H_{26}N_4O_8S$) is odorless white crystals or crystalline powder having a melting point of from 150° to 155° C.; naphamostat mesilate is white crystalline powder having melting point of about 260° C. (decomposed). Among these inhibitors, there may be some which specifically inhibit the biologically active protein used in the present invention, and they can not be used together with such a biologically active protein. For example, naphamostat mesilate selectively and strongly inhibits trypsin, callidinogenase and thorombin and can not be used together with these proteins. However, naphamostat mesilate does not inhibit insulin and therefore can be used together with insulin. This can easily be determined by those skilled in the art. In the present invention, the effects of the present invention can further be increased by incorporating such a inhibitor.

The composition of the present invention may be administered in the form of a formulation for oral or local administration In the present invention, the local administration is meant for e.g. intravencus, subcutaneous, perctaneous, oral, pernasal, or intestinai administration. Formulations for local administration include, for example, injection drugs, tablets, capsules, powders, granules, troaches, sapositories, ointments, creams or lotions, gels, spray formulations and aerosols. In the case of oral administration, the composition must be in an enteric form. These formulations for administration may be prepared by conventional methods well known to those skilled in the art. For example, in the case of tablets or capsules, conventional additives including a binder such as a saccharide solution, gum arabic, gelatin, sorbitol, tragacanth gum or polyvinyl pyrrolidone; a filler such as lactose, sugar, corn starch, calcium phosphate, sorbitol or glycin; a tabletting lubricant such as magnesium stearate; a disintegrator such as starch, polyvinyl pyrrolidone, sodium starch glycolate or fine crystalline cellulose; and a wetting agent such as sodium lauryl suifate, may be used to prepare desired formulations by such an operation as mixing, packing, tabletting or enteric coating. The composition of the present invention usually contains from 0.1 to 99% by weight of the active ingredient. The composition of the present invention is used for the treatment of a disease for which the contained biologically active protein is effective. For example, in the case of insulin, it is used for treatment of diabetes for which insulin treatment is effective. Likewise, interferon a is used for the treatment of kidney cancer and multiple myeloma; calcitonin is useful for reducing the pain or bone decrease by osteoporosis and for treating hypercalcemia and bone Paget's disease; and callidinogenase is useful mainly for the treatment of circulatory disorders.

The dose of the composition of the present invention varies depending upon the degree of the desease or the body weight of the patient. Generally, it is such an amount that the biologically active protein contained in the composition provides sufficient effectiveness. For example, in the case of insulin, the dose is usually from 4 to 60 units per administration and at most 200 units per day. The amount of the protease inhibitor is usually from 10 to 100 mg per administration and from 20 to 1,000 mg per day. The administration is conducted preferably at least once, for example, a few times, per day.

With the composition of the present invention, no toxicity is observed with the dose within the above-mentioned range.

The composition of the present invention makes it possible to administer a biologically active protein which used to be administered only by injection, not only by injection but also by oral and local administration. For example, when the composition is orally administered, the absorption rate is fast, and the maximum absorbed concentration is high. Besides, it makes it possible to obtain an excellent effect such that the concentration in the body can be maintained for a long period of time. Further, in the case of a limited number of biologically active proteins which are considered to be feasible for oral or local administration, the composition of the present invention provides a high absorption rate and a high maximum absorbed concentration and presents a merit that the concentration in the body can be maintained for a long period of time, as compared with such conventional products. These advantages have not been obtained by the conventional products.

Now, the present invention will be described in further detail with reference to Examples. However, it should be understood that the present invention is by no means restricted by such specific Examples.

EXAMPLE 1

To an aqueous solution (100 μl) of 2-(6-aminocaproyl)lysolecithin (in the formula (III), $R^1$ is a pentamethylene group, $Z'$ is —$NH_2$, and $R^1$ in B is a palmitoyl group) (0.0045 g, 0.006 mmol), 4.2 μl of a solution of cyanuric chloride (61 g) in DMF (0.2 ml) was added under cooling with ice. The pH was adjusted to pH6.5–7.0 with sodium carbonate, and the mixture was stirred for 1 hour. To the mixture, IgG (1 mg, in a phosphate buffer solution, 332 μl) was added, and the mixture was stirred at room temperature overnight while maintaining the pH at 7.0, to obtain IgG lecithin.

EXAMPLE 2

To the aqueous solution of 2-(6-aminocaproyl)-lysolecithin (100 ml, 0.006 mmol) as used in Example 1, IgG (1 mg, in a phosphate buffer solution, 332 µl) was added. Further, EDC (1.3 mg) and sugar (2 mg) were added thereto, and the mixture was incubated at 25° C. for 2 hours and then left to stand overnight at neutral. Then, the mixture was dialyzed with PBS at 4° C., to obtain IgG-lecithin.

EXAMPLE 3

Test for biological activities (I) The cell affinity of the substance of the present invention was examined by the following method.

(A) From human peripheral blood (25 ml), erythrocytes and lymphocytes were separated by means of Ficoil Paque and respectively suspended in RPMI 1640 (10% FCS added). To each of them, [$^{125}$I]IgG-lecithin (10 µg as IgG) was added, and the mixture was incubated at 37° C. for 3 hours and then washed 4 times with a physiological saline solution, whereupon the amount of IgG bonded to or taken in the cells, was counted.

In the same manner, an experiment was conducted by using [$^{125}$I]IgG alone, or a mere mixture of lecithin and [$^{125}$I]IgG.

The affinity to lymphocite of IgG-lecithin obtained in each Example was as shown below. In this case, an experiment was conducted also with respect to lipid microspheres containing the same amount of IgG.

| Sample | Uptake amount (%) |
|---|---|
| Product of Example 1 | 0.84 |
| Product of Example 2 | 0.91 |
| Free IgG | 0.43 |
| Lecithin + IgG | 0.32 |
| IgG microspheres | 0.69 |

(B) The affinity of erythrocytes of IgG-lecithin obtained in each Example was as follows.

| Sample | Uptake amount (%) |
|---|---|
| Product of Example 1 | 2.1 |
| Product of Example 2 | 2.2 |
| Free IgG | 1.69 |
| Lecithin + IgG | 1.0 |

It is apparent from the above results that the products of the present invention are excellent in the affinity to cells as compared with the corresponding free biologically active protein or a mere mixture of such a protein and lecithin. (II) The transmigration of the substance of the present invention to a diseased arterial site was examined by the following method.

To SHR-SP rats (16 weeks old, male, Wister species), [$^{125}$I]IgG-lecithin (solvent: PBS) was intravenously administered in an amount of 100 µg/rat as IgG. Three hours later, the blood was removed, and the aorta was extracted, whereupon the amount of [$^{125}$I]IgG taken in the artery was counted.

On the other hand, a similar experiment was conducted by using normal rats and free [$^{125}$I]IgG.

The results were as shown below.

| Type of rats | Uptake amount (%) |
|---|---|
| IgG-Lecithin | |
| SHR | 0.56 |
| Normal | 0.29 |
| IgG | |
| SHR | 0.24 |
| Normal | 0.32 |

It is apparent from the above results that the substance of the present invention is taken in the diseased arterial site in a large amount and thus provides excellent pharmacological effects. (III) The affinity of the substance of the present invention to cancer cells, was examined.

MM46 cancer cells were suspended in RPMI 1640 (10% FCS added) to a concentration of $2 \times 10^6$ cells/ml, and [$^{125}$I]IgG-lecithin was added thereto to bring the concentration to a level of 10 µg/ml as IgG. The mixture was incuvated at 37° C. for 3 hours, and then washed with a physiological saline solution, whereupon the amount of IgG bonded to or taken in the MM46 cancer cells was counted.

Separately, a similar experiment was conducted by using [$^{125}$I]IgG alone.

| Sample | Uptake amount (%) |
|---|---|
| IgG-lecithin | 7.5 |
| IgG | 1.0 |

It is apparent from the above results that the substance of the present invention is taken in the cancer cells in a very large amount. (IV) Then, the distribution in the body of the substance of the present invention was examined.

Using C$_3$H mice (male, 22–25 g), [$^{125}$I]IgG-lecithin (solvent: PBS) was intravenously administered to bring the-concentration of IgG to a level of 50 µg/mouse. Three hours later, each mouse was killed, and the distribution to each organ in the body was examined.

On the other hand, similar experiments were conducted by using [$^{125}$I]IgG alone, a mere mixture of $^{125}$I]IgG and lecithin, or [$^{125}$I]IgG liquid microspheres.

The results are shown below.

| Samples | Uptake amount (%) | | | | |
|---|---|---|---|---|---|
| | Lung | Heart | Kidney | Liver | Spleen |
| IgG — Lecithin | 2.2 | 1.8 | 1.4 | 8.3 | 2.8 |
| IgG | 1.1 | 1.7 | 0.5 | 0.6 | 0.8 |
| IgG + Lecithin | 0.6 | 1.1 | 0.4 | 0.8 | 0.2 |
| IgG microspheres | 0.8 | 1.6 | 0.8 | 0.9 | 0.4 |

It is apparent from the above results that the substance of the present invention is excellent in the uptake to each organ. Particularly, it can be said that the substance of the present invention is particularly excellent in the uptake to the liver. These experimental results indicate that with the substance of the present invention, the distribution in a living body and the affinity to cells are remarkably different, and thus an improvement of the pharmacological activities of biologically active proteins, a reduction of side effects and acceleration of the absorption can be expected.

Further, as shown by the results of (I) to (IV), the substance of the present invention exhibits excellent and different physical properties as compared with the corresponding biologically active protein or a mere mixture of such a protein and lecithin. This indicates that lecithin and the biologically active protein are bonded by a covalent bond.

EXAMPLE 4

30 mg (0.04 mmol) of amino lecithin of the formula (III), (in the formula (III), Z' is t-BocNH, and the carbon number of $R^1$ is 5) was treated with 0.5 ml of TFA to remove Boc, and after completely distilling off TFA, dissolved in distilled water and neutralized with $Na_2CO_3$. Then, 5 mg (0.0008 mmol) of insulin was added thereto, and 1-ethyl 3-(3-dimethylaminopropyl)carbodiimide (EDC) was added so that the final concentration would be 0.1M. The mixture was stirred overnight at room temperature.

Rats (Wister species, male, 250 g) were subjected to celiotomy, and a mixture comprising 30 or 100 units/μg of lecithin-modified insulin and $10^{-3}M$ of naphamostat mesilate was administered to the duodenum. Separately, as control, a mixture comprising 100 units/kg of insulin and $10^{-3}M$ of mecyl acid naphamostat, was administered. The blood sugar values upon expiration of 0, 30, 60, 90, 120 and 180 minutes after the administration were measured. The results are shown in Table 1.

TABLE 1

| | Blood sugar value (mg/dl) | |
|---|---|---|
| | Lecithin-modified insulin (units/kg) | Control (units/kg) |
| Time (min) | 30 | 100 | 100 |
| 0 | 61 | 60 | 65 |
| 30 | 116 | 101 | 113 |
| 60 | 112 | 57 | 114 |
| 90 | 89 | 65 | 105 |
| 120 | 83 | 64 | 111 |
| 180 | 84 | 79 | 119 |

It is apparent from Table 1 that the blood sugar value of the control did not substantially change, and no effects were observed, whereas with the composition of the present invention, adequately excellent effects were observed even in an amount of ⅓ of the control. Further, the effects can be maintained over a long period of time.

EXAMPLE 5

Lecithin-modified callidinogenase was prepared in the same manner as in Example 4 using 5 mg of the amino lecithin of the formula (III) as used in Example 4 and 250 μg of [$^3$H]-callidinogenase.

In the same manner as in Example 4, 60 μg/10 μl of [$^3$H] lecitin-modified callidinogenase was administered to rats in an amount of 200 μl per rat. Further, as control, [$^3$HI callidinogenase was administered in the same manner.

The concentration of [$^3$H]-callidinogenase in the blood was measured upon expiration of 30, 60, 90, 120 and minutes after the administration. The results are shown in Table 2.

TABLE 2

| | % Relative to the administered callidinogenase | |
|---|---|---|
| Time (min) | Lecithin-modified | Control |
| 30 | 2.20 | 0.50 |
| 60 | 2.68 | 1.32 |
| 90 | 2.61 | 2.06 |
| 120 | 1.98 | 1.68 |

TABLE 2-continued

| | % Relative to the administered callidinogenase | |
|---|---|---|
| Time (min) | Lecithin-modified | Control |
| 180 | 1.48 | 1.35 |

Callidinogenase has been used not only as an injection drug but also for oral administration as an enteric drug. Whereas, it is apparent from Table 2 that with the composition of the present invention, the absorption rate is fast, the maximum absorbed concentration is high, and it has additional merit that the concentration in the body can be maintained over a long period of time.

EXAMPLE 6

Synthesis of 2-(4-hydroxycarbonylbutyroyl)lysolecithin-introduction of lecithin

To a suspension of 204 mg (0.4 mmol) of lysolecithin having a hydroxyl group at the 2-position of glycerol (R in B is a palmitoyl group, the same applies hereinafter) in chloroform-pyridine (8 ml/2 ml), 98 mg (0.8 mmol) of DMAP (N,N-dimethylaminopyridine) and 91 mg (0.8 ml) of glutaric anhydride were added, and the mixture was stirred at 60° C. for 15 hours. The reaction solution was cooled and concentrated under reduced pressure. To the concentrated residue, a mixture of chloroform:methanol:water=4:5:1 (2 ml) was added and dissolved, and passed through an ion exchange column (Dowex 50W-X8) impregnated with the same liquid. The desired compound was fractionated by TCL and concentrated under reduced pressure, and the residue was purified by silica gel column. 225 mg (0.36 mmol, 90%).

$^1$H-NMR(CDCL$_3$) 0.84(t,3H), 1.20(brs),
1.52–1.60(brs,2H), 1.80–1.95(m,2H), 2.20–2.42(m,6H),
3.35(s,9H), 3.78(m,4H), 3.90–4.35(m,4H), 5.20(s,1H).

EXAMPLE 7

Synthesis of an active ester of 2-(4-hydroxycarbonylbutyroyl)lysolecithin 225 mg (0.36 mmol) of the carboxylic acid obtained in Example 6 was dissolved in 5 ml of DMF (N,N-dimethylformamide). The solution was cooled to 0° C., and 41 mg (0.36 mmol) of N-hydroxysuccinimide and 74 mg (0.36 mmol) of DCC (dicyclohexylcarbodiimide) were added thereto. The mixture was adjusted to pH6–7 with triethylamine and stirred at room temperature for 15 hours. Insoluble substances were filtered off by celite to obtain a DMF solution of the active ester.

EXAMPLE 8

Synthesis of an active ester of 2-(4-hydroxycarbonylbutyroyl)lysolecithin 225 mg (0.36 mmol) of the carboxylic acid obtained in Example 6 was dissolved in 5 ml of dichloromethane. The solution was cooled to 0° C., and 41 mg (0.36 mmol) of N-hydroxysccucinimide and 74 mg (0.36 mmol) of DCC were added thereto. The mixture was adjusted to pH6–7 with triethylamine and stirred at room temperature for 15 hours. In soluble substances were filtered off by celite to obtain a dichloromethane solution of the active ester.

EXAMPLE 9

Synthesis of 2-[N-(2-hydroxycarbonylpropionyloxy)-6-aminocaproyl]lysolecithin

To the same suspension of 234 mg (0.32 mmol) of 2-(6-aminocaproyl)lysolecithin in chloroform-pyridine (8 ml/2 ml) as used in Example 1, 177 mg (0.96 mmol) of DMAP and 96 mg (0.96 mmol) of succinic anhydride were added, and the mixture was stirred at 60° C. for 15 hours. The reaction solution was cooled and concentrated under reduced pressure. To the concentrated residue, a mixture of chloroform:methanol:water=4:5:1 (2 ml) was added and the residue was dissolved. The solution was passed through an ion exchange column (Dowex 50W-X8) impregnated with the same liquid. The desired product was fractionated by CLC and concentrated under reduced pressure. Then, the residue was purified by silica gel column. 134 mg (0.19 mmol, 58%).

1H-NMR(CDCL$_3$) 0.87(t,3H), 1.20(brs), 1.45–1.60(m,8H),
2.40(t,4H), 2.40–2.60(brs,4H), 3.10(brs,2H), 3.24(s,9H), 3.67(brs,2H), 3.93(m,2H), 4.05–4.20(m,4H), 5.20(m,2H).

EXAMPLE 10

Synthesis of an active ester of 2-[N-(3-hydroxycarbonylpropionyloxy)-6-aminocapropyl]lysolecithin 134 mg (0.19 mmol) of the carboxylic acid obtained in Example 9 was dissolved in 5 ml of dichloromethane, and the solution was cooled to 0° C. Then, 22 mg (0.19 mmol) of N-hydroxysccucinimide and 39 mg (0.19 mmol) of DCC were added thereto. The mixture was adjusted to pH6–7 with triethylamine and stirred at room temperature for 15 hours. Insoluble substances were filtered off by celite to obtain a dichloromethane solution of the active ester.

EXAMPLE 11 (Lecithin-modification)

The solvent of the active ester lecithin was evaporated, and SOD dissolved in 0.1M borate buffer was added. The mixture was reacted at 0° C. for 1 hour and at room temperature for further 2 hours, and then dialyzed against distilled water. This solution was used by itself for the subsequent measurements.

Number of lecithin introduced to SOD and residual activities ② In the case of human SOD in Vitro

| Number of lecithin introduced to SOD and residual activities ② In the case of human SOD in Vitro | | |
|---|---|---|
| Mol ratio | Number of lecithin introduced | Residual activities |
| Compound of Example 7 | | |
| × 1.2 | 5.7 | 83% |
| × 1.2 | 6.2 | 66% |
| × 1.2 | 8.3 | 74% |
| × 2.4 | 5.3 | 74% |
| × 2.4 | 12.7 | 65% |
| × 2.4 | 14 | 39% |
| × 4.8 | | |
| Compound of Example 10 | | |
| × 1.2 | 3 | 108% |
| × 1.2 | 3 | 78% |
| × 2.4 | 4.5 | 73% |
| × 4.8 | 4.0 | 61% |

EXAMPLE 12

Effects to Burned Mice

The hair was removed from the back of the C$_3$H mouse, and an electric iron heated to 400° C. was pressed against the back for 10 seconds to obtain a burned mouse.

Lecithin-modified SOD was intravenously administered immediately prior to the burning and 30 minutes after the burning. The degree of healing was compared between a non-treated group and a group treated by the lecithin-modified SOD. The degree of healing was evaluated by adding +every time when one of the following conditions has been satisfied.
① The wound is dry.
② An eschar has formed.
③ The area of the burn has reduced.
④ The hair has started to grow around the burn.
Results

| | When treated | 3 hrs later | One day later | 4 days later | 7 days later |
|---|---|---|---|---|---|
| Non-treated group | − | − | + | + | + |
| Group treated with the lecithin-modified SOD | − | + | ++ | +++ | ++++ |

| Number of lecithin introduced to SOD and residual activities | | |
|---|---|---|
| ① In the case of Bovine SOD | | |
| Amount of lecithin used for reaction Number of —NH$_2$ in SOD | Number of lecithin introduced per mol of SOD, as measured by TNBS method | Xanthine, Xanthine oxide Residual activities |
| Compound of Example 7 | | |
| × 1.2 times mol | 10.4 | 69% |
| × 1.2 | 7.5 | 73% |
| × 1.2 | 7.3 | 82% |
| × 2.4 | 14 | 56% |
| × 2.4 | 11 | 76% |
| × 4.8 | 14 | 56% |
| × 4.8 | 14 | 54% |
| Compound of Example 10 | | |
| × 1.2 | 5 | 88 |
| × 1.2 | 3 | 101 |
| × 1.2 | 6 | 103 |
| × 2.4 | 7 | 75 |

As shown above, healing was significantly quick with the group treated with the lecithin-modified SOD as compared with the non-treated group.

What is claimed is:

1. A biologically active protein composition for oral or local administration, which comprises
a modified biologically active protein consisting essentially of a biologically active protein covalently bonded to lecithin and a protease inhibitor which does not inhibit said modified biologically active protein.

2. The biologically active protein composition according to claim 1, wherein the biologically active protein is an antibody.

3. The biologically active protein composition according to claim 1, wherein the biologically active protein is superoxide dismutase.

4. The biologically active protein composition according to claim 1, wherein the biologically active protein is insulin.

5. The biologically active protein composition according to claim 1, wherein the biologically active protein is callidinogenase.

6. The biologically active protein composition according to claim 1, which is represented by the formula (I):

$$A(X-B)_k \qquad (I)$$

wherein A is a residue of the biologically active protein, B is a residue of lysolecithin bonded to X by a hydroxyl group at the 2-position of glycerol, with the hydrogen atom of said hydroxyl group removed, X is a covalent linking group, and k is a bond number of at least 1.

7. The biologically active protein composition according to claim 6, wherein X is

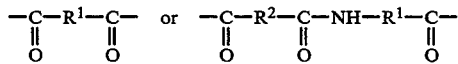

wherein each of $R^1$ and $R^2$ is an alkylene group.

8. The biologically active protein composition according to claim 6, wherein A is the residue of an antibody.

9. The biologically active protein composition according to claim 6, wherein A is the residue of superoxide dismutase.

10. The biologically active protein composition according to claim 6, wherein A is the residue of insulin.

11. The biologically active protein composition according to claim 6, wherein A is the residue of callidinogenase.

* * * * *